United States Patent [19]

Salibello et al.

[11] Patent Number: 5,325,136

[45] Date of Patent: Jun. 28, 1994

[54] COMPUTER DISPLAY SCREEN SIMULATION FOR OPTOMETRIC EXAMINATION

[75] Inventors: Cosmo Salibello; Jonathan G. Torrey, both of Portland, Oreg.

[73] Assignee: PRIO Corporation, Portland, Oreg.

[21] Appl. No.: 211

[22] Filed: Jan. 4, 1993

Related U.S. Application Data

[63] Continuation-in-part of Ser. No. 665,903, Mar. 7, 1991, Pat. No. 5,191,367, which is a continuation-in-part of Ser. No. 282,596, Dec. 12, 1988, Pat. No. 4,998,820.

[51] Int. Cl.$^5$ .............................................. A61B 3/02
[52] U.S. Cl. .................................... 351/243; 351/203; 351/239
[58] Field of Search ...................... 313/483; 428/917; 351/203, 233, 239, 240, 243, 246, 224, 225, 239, 243, 244

[56] References Cited

U.S. PATENT DOCUMENTS

| | | | |
|---|---|---|---|
| Re. 28,921 | 8/1976 | Haines et al. | 351/243 |
| 2,180,652 | 11/1939 | Wilson | 351/237 |
| 2,282,494 | 5/1942 | Potter | 351/233 |
| 2,853,919 | 9/1958 | Richards | 351/246 |
| 4,212,520 | 7/1980 | Klimsa | 351/243 |
| 4,239,351 | 12/1980 | Williams et al. | 351/242 |
| 4,285,580 | 8/1981 | Murr | 351/224 |
| 4,412,729 | 11/1983 | Hartmann | 351/239 |
| 4,421,392 | 12/1983 | Crick et al. | 351/224 |
| 4,511,228 | 4/1985 | von Gierke et al. | 351/243 |
| 4,550,990 | 11/1985 | Trispel et al. | 351/243 |
| 4,564,278 | 1/1986 | Clark | 351/233 |
| 4,572,630 | 2/1986 | Task et al. | 351/243 |
| 4,576,454 | 3/1986 | Charney et al. | 351/243 |
| 4,611,893 | 9/1986 | Schrier | 351/239 |
| 4,764,007 | 8/1988 | Task | 351/243 |
| 4,998,820 | 3/1991 | Salibello et al. | 351/243 |
| 5,191,367 | 3/1993 | Salibello et al. | 351/243 |

FOREIGN PATENT DOCUMENTS

3133608A1 8/1981 Fed. Rep. of Germany.

*Primary Examiner*—William L. Sikes
*Assistant Examiner*—David R. Parsons
*Attorney, Agent, or Firm*—Marger, Johnson, McCollom & Stolowitz

[57] ABSTRACT

An improved vision tester apparatus and method are disclosed for use in conducting optometric examinations of patients who use video display terminals (VDTs). Specifically, the tester simulates images that are displayed to the patient by a typical VDT, so as to facilitate prescribing corrective lenses that will perform well for the patient when used with an actual VDT. The tester (10) includes a flat-panel electroluminescent light source (32) for illuminating a screen (14) without hot spots. The screen includes a colored ink layer (78,80,82) and an opaque ink mask (70) for forming pixel-like light elements (24). Lensing structures (52,56,58,60) degrade the image such that each light element exhibits a generally Gaussian light amplitude curve (FIG. 5B) characteristic of a pixel of an actual VDT. A rechargeable battery (34) coupled to a inverter circuit (30) provide portable power for the EL panel to complete a compact, portable tester.

26 Claims, 4 Drawing Sheets

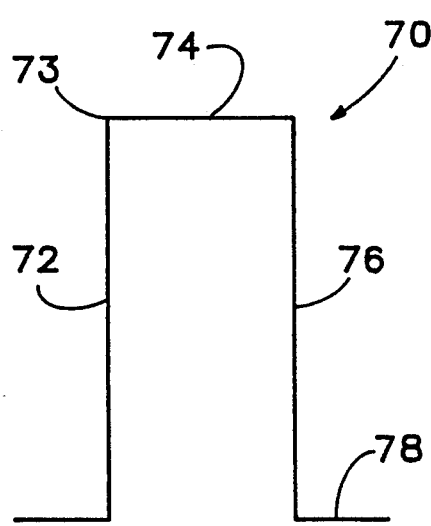
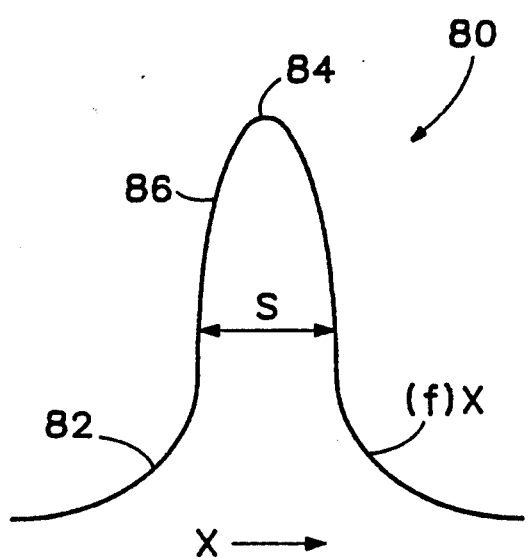
FIG. 5A
(PRIOR ART)
FIG. 5B

COMPUTER DISPLAY SCREEN SIMULATION FOR OPTOMETRIC EXAMINATION

This application is a continuation-in-part of co-pending application Ser. No. 07/665,903, filed Mar. 7, 1991 now U.S. Pat. No. 5,191,367 which is a continuation-in-part of application Ser. No. 07/282,596, filed Dec. 12, 1988, now U.S. Pat. No. 4,998,820.

BACKGROUND OF THE INVENTION

The present invention relates to vision testing equipment and more specifically to instruments and methods for use in conducting optometric examinations.

As use of the video display terminal ("VDT") has become more widespread, for example in connection with computers, so too have certain ophthalmological problems associated with its use become more common. A recent survey of optometrists, reported in the J. Am. Optom. Assoc. 1992 (vol. 63, pp 687-92), shows that more than 14% of optometric patients present with symptoms primarily associated with use of the VDT, or almost 10 million examinations annually when projected to the U.S. population. Responding optometrists were unable to confidently arrive at a diagnosis and treatment more frequently for VDT patients (20.87%) compared to non-VDT patients (14.05%).

Alphanumeric characters displayed on video display screens are made up of dots or pixels which do not have well defined borders and therefore are difficult for the eye to focus upon. Further, since video screens are maintained at a constant distance of about 50 cm from the user's eyes, the same eye muscles are in constant use in focusing on the screens. These factors cause significant amounts of stress and fatigue on the eyes of video display terminal users which are often aggravated by the fact that many such users utilize their computers for extended periods on a daily basis. The stress associated with video display use frequently results in peculiar types of eye problems requiring special corrective prescriptions in the spectacles selected for the users suffering from these problems.

In order to accurately diagnose these problems, appropriate test equipment and test procedures must be provided. In accordance with the process currently used by medical practitioners to determine the spectacle requirements of typical patients, an apparatus (phoropter) is placed in front of the eyes of the patient which enables the doctor to rapidly change a wide selection of lenses while the patient views a set of test images through the lens changing apparatus. As the patient focuses on the test images, the doctor assesses the status of the muscles inside the patient's eyes and judges their degree of relaxation through the use of a retinoscope. The doctor determines the combination of lenses and the prescription best suited to the patient by changing the lenses until he detects the combination which provides the most relaxed state in the eye muscles of the patient.

As may be understood from the above, the fitting of corrective lenses is basically a trial and error process in which the doctor observes the reaction of the patient's eye muscles to an appropriate test image for various combinations of lenses. However, without a test image which accurately simulates the conditions under which the patient may experience eye problems, a prescription for suitable corrective lenses may not be reliably determined. When presented with an image which does not have sharply defined edges or which is slightly out of focus, the eye will respond by reverting to a level of tonic muscle activity known as the resting point of accommodation, having a focal length with a sharply defined image placed at the same distance from the eye. Accordingly, the prescription required for eyeglasses used with a video display terminal can differ from a prescription for use in viewing printed material.

Commercially available equipment and clinical protocols do not provide a satisfactory system for generating test images which simulate the characteristics of video display terminals such as computer screens. Consequently, most practitioners have no recourse but to make educated guesses as to the lens corrections which may work best for their patients. After the patients go back to work and try the new prescriptions, many return because their glasses are not suitable. Testing is repeated, and a new prescription may be tried. This is, however, a time consuming, expensive, inaccurate and generally unsatisfactory method of proceeding to provide spectacle prescriptions for computer users.

It is therefore an object of the present invention to provide an improved system for testing the vision of video display terminal users which allows for accurate determination of the best corrective lens prescriptions for such patients.

It is another object of the present invention to provide an improved system for testing the vision of video display terminal users which allows for accurate determination of the best corrective lens prescription for such patients.

It is another object of the present invention to provide an improved apparatus which accurately simulates alphanumeric characters as presented on a video display screen and which can be conveniently used in accordance with current optometric test procedures.

It is a further object of the present invention to provide an improved optometric instrument for use in determining prescriptions for corrective lenses which is economical, reliable, compact and simple to use.

SUMMARY OF THE INVENTION

The present invention comprises an optical instrument for use in optometric examinations which simulates the optical features of alphanumeric displays typically provided by video display terminals. The instrument comprises an electro-luminescent panel light source and a multi-layered screen through which light from the source may be directed to a patient viewing the screen. The screen comprises a printed layer including sets of small openings or pixels which cooperatively define alphanumeric characters in terms of pixel-like elements of light from the light source. The screen further comprises a mechanism for degrading the alphanumeric character images by reducing the higher spatial frequencies of light associated with the light elements which define the characters.

In the preferred embodiment, the screen includes a lensing structure made of layers of plastic sheet materials having different indexes of refraction which refract the light from the light elements and provide said light elements with substantially Gaussian profiles characteristic of the pixels formed by video display terminals. In operation, the light elements and lensing structure work together to generate an alphanumeric character display which accurately simulates the characteristics of the displays provided by video display terminals for the purpose of optometric examination and diagnosis.

In a preferred embodiment, our improved vision tester apparatus is constructed within a generally flat, rigid housing. A flat EL panel light source is built into the housing for providing illumination toward the front of the housing. A generally flat screen is arranged within the housing over the EL panel so that the EL panel illuminates the screen. A bezel extends around the front of the housing overlapping a periphery of the screen so as to secure the screen in place within the housing. Finally, a rechargeable power supply is provided in the housing for powering the EL panel to illuminate the screen.

The screen includes a polycarbonate cover layer and an intermediate polycarbonate layer interposed between the EL panel and the polycarbonate cover layer. Bonding layers are formed between the intermediate and cover polycarbonate layers, and between the intermediate layer and the EL panel. Light elements together forming an image for display to a patient are formed by a mask deposited on one side of the intermediate polycarbonate layer facing the EL panel. The mask is preferably formed by a thin layer of substantially opaque ink having a plurality of pixel openings in it for transmitting light from the EL panel through the intermediate polycarbonate layer. The light elements proceed through the polycarbonate cover layer so as to form corresponding pixels as seen by a patient facing the screen, as if the patient was observing an VDT image. An additional layer of translucent, tinted ink may be applied over the ink mask for coloring the pixels to simulate the color of a VDT image.

The foregoing and other objects, features and advantages of the invention will become more readily apparent from the following detailed description of a preferred embodiment which proceeds with reference to the drawings.

BRIEF DESCRIPTION OF THE DRAWINGS

FIG. 5A is a square-wave light amplitude curve representative of printed matter and testing devices of the prior art.

FIG. 5B is a generally Gaussian light amplitude curve produced by a video display terminal and by the present invention.

DETAILED DESCRIPTION OF THE PREFERRED EMBODIMENT

Figure 1:
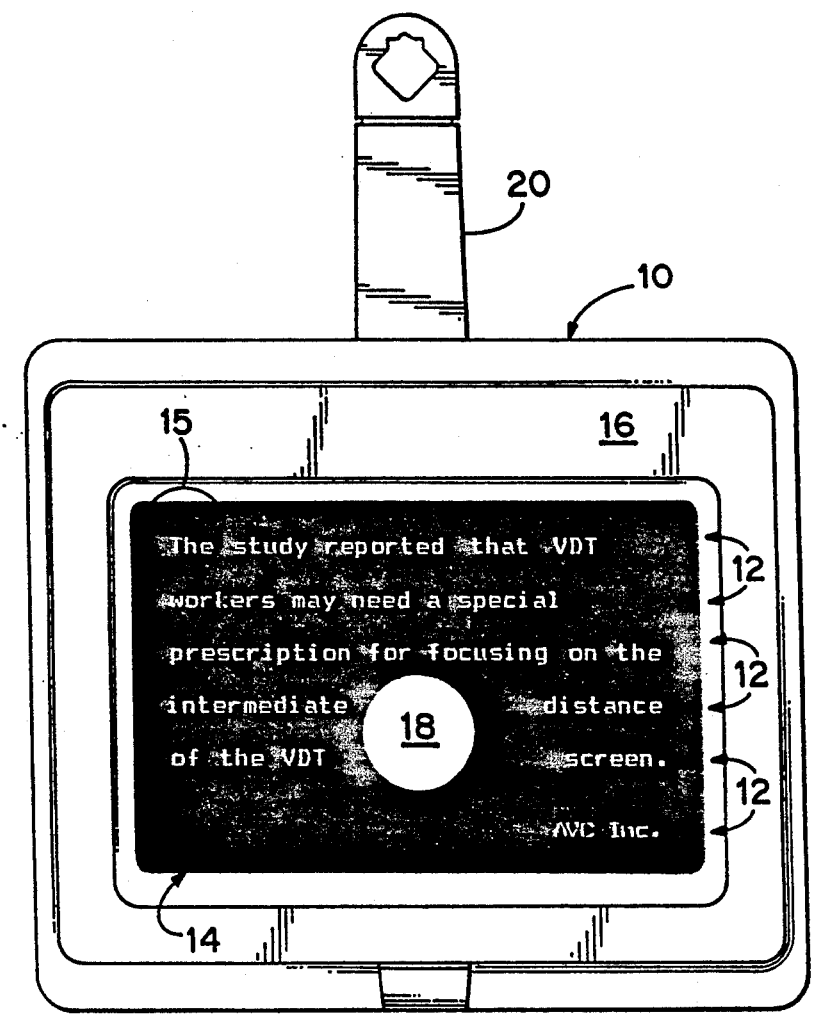
FIG. 1 is a front view of a tester apparatus corresponding to one embodiment of the present invention and showing a display of alphanumeric characters on the screen.

Referring now to FIG. 1, the apparatus of 10 for simulating a video display terminal ("VDT") constitutes an embodiment of the present invention in which six lines 12 of alphanumeric characters are provided for viewing by a patient during an optometric examination. The actual characters or text selected for display is not critical. The lines 12 are presented on a multi-layered screen 14 which is mounted in a rigid housing 16. A viewing tunnel 18 allows the medical practitioner conducting the optometric exam to directly view the patient's eyes from behind the apparatus 10 during the course of the examination, while a support arm 20 allows the apparatus 10 to be conveniently mounted and readily swung into position for use when desired.

Optionally, a conventional printed eye-chart, test card or the like (not shown) may be mounted on the back side of the tester housing. By rotating the tester about a vertical axis, the back side eye-chart may be brought into the patient's line of sight. This would enable the optometrist to utilize the printed eye-chart or test card as part of her testing protocol as desired without having to fumble with additional apparatus for mounting the eye-chart in front of the patient. A rotational joint (not shown) may be provided within the support arm 20 or interconnecting the support arm 20 and the housing 16 for this purpose. If the dimensions of the eye-chart are such as would occlude the viewing tunnel, the chart should have a suitable cutout or aperture to avoid that problem. Eye-charts or the like may be removably attached to the back of the housing, for example by provision of one or more slots along peripheral edges of the back of the housing, sized to receive the eye-chart. This has the advantage of permitting easy substitution of various eye-charts as needed. Alternatively, a selected eye-chart may be more permanently attached to the housing so it is always readily available.

Figure 2:
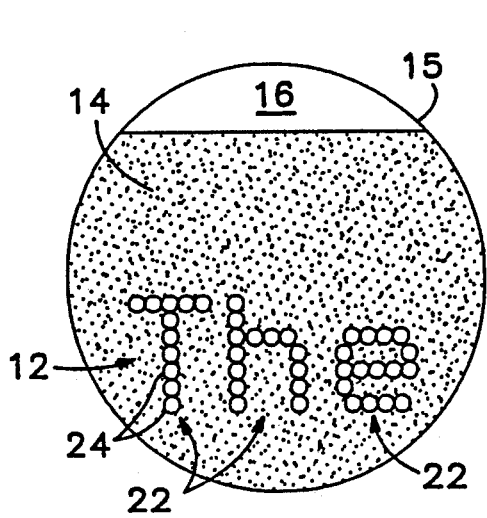
FIG. 2 is an enlarged view of a portion of the screen of FIG. 1 illustrating how each alphanumeric character is formed by a series of light elements or pixels.

As shown by FIG. 2, which provides a close-up view of the region within the circle 15 in FIG. 1, the alphanumeric characters 22 are made up of sets of pixel-like elements 24 disposed in 7×9 matrices in a manner similar to the characters displayed on many video display terminals.

Figure 3:
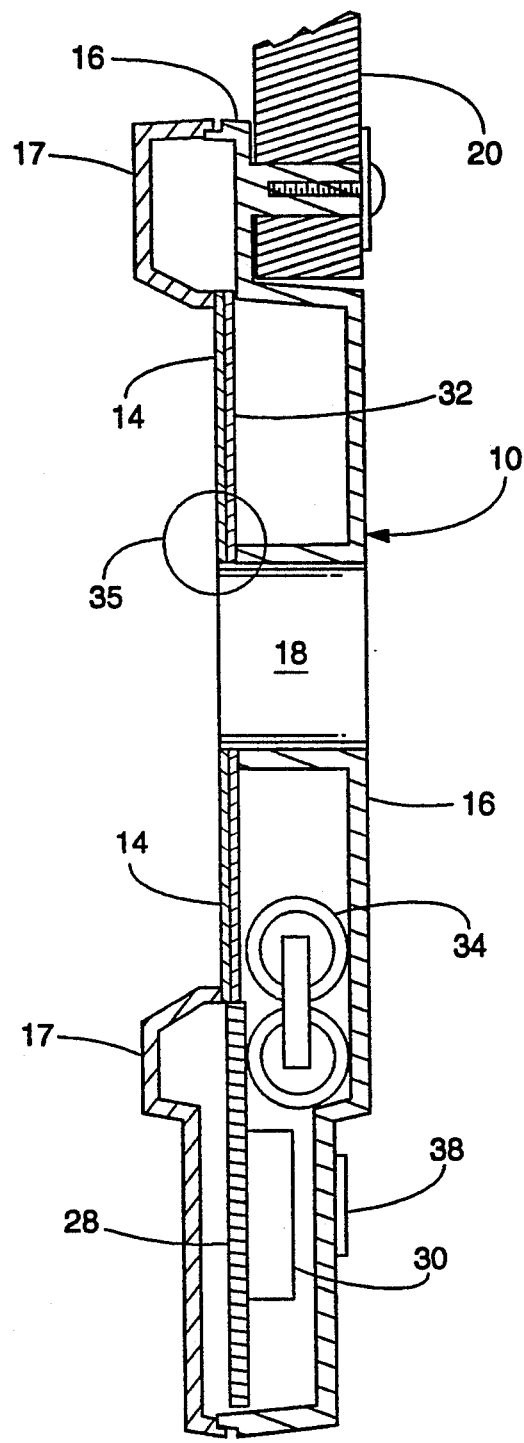
FIG. 3 is a cross sectional side view of the apparatus of FIG. 1 illustrating the operative components associated with the present invention.

Referring now to FIG. 3, the VDT simulation apparatus 10 is shown in cross-section. The apparatus comprises a housing 16 through which the viewing tunnel 18 is formed. The housing includes a shelf for supporting a generally flat, thick-film electro-luminescent (EL) panel 32. EL panel 32 includes an approximately central aperture sized consistent with and registered about the viewing tunnel 18. The EL panel provides illumination directed forwardly through the screen 14. A suitable EL panel is commerically available, for example, from Loctite Luminescent Systems, Inc. of Lebanon, NH (Part No. LSI RH) or from NEC/World Products Inc. of Sonoma, Calif. (Part No. NEL-5LB-574-W). A bezel 17 surrounds the screen 14 and secures it in place against the EL panel, the bezel being connected along its perimeter to the housing 16.

The EL panel is preferred as it provides a uniform, consistent, color-balanced light source for the screen. The light emitted by the EL panel is much closer to natural light in spectral content than light bulbs. Importantly, the intensity of the emitted light is uniform across the EL panel face. Since it does not exhibit "hot spots" the resulting display more closely simulates video display screens. Since the EL panel provides uniform light intensity, the diffuser taught in U.S. Pat. No. 4,998,820 is unnecessary. Electro-luminescence is a solid-state phenomenon, that uses phosphors, rather than heat, to generate light. It is, therefore, also more efficient than light bulbs, resulting in battery life on the order of three times that expected when driving light bulbs in a similar application. Because the EL panel is solid-state it is also highly reliable and virtually immune to mechanical shock.

The EL panel requires a power supply that delivers a high frequency, low amperage, AC signal, for example 115 VAC at approximately 500 Hz. To provide the required power, in a small, reliable package, a battery pack 34 is used to first provide a DC power source. Preferably, the DC power source comprises a NiCad battery pack of four 1.2 volt, 500 mA-hr batteries wired in series. The battery pack thus provides a nominal 4.8 volts DC. A polyswitch solid-state current limiter 38 is interposed in the series of batteries for protection against short circuits. Suitable batteries are available commercially as Panasonic P-50 AA/FT, for example. A suitable current limiter is Raychem PTC SRP-200 or a similar device. A complete battery pack well suited to the present purpose is manufactured by Micro Power Electronics of Beaverton, Oreg. Preferably, means are further provided for recharging the DC power source, details of which are known.

The DC power source is coupled to an "inverter" circuit 30 to convert the DC power to 115 VAC, 500 Hz power. A suitable inverter is commercially available from NEC (Part No. NEL-D32-49) or from Loctite (Part No. 300 series LSI X-020). The foregoing electronic circuitry preferably is arranged on a printed circuit board 28 or the like for reliability and ease of construction.

Figure 4:
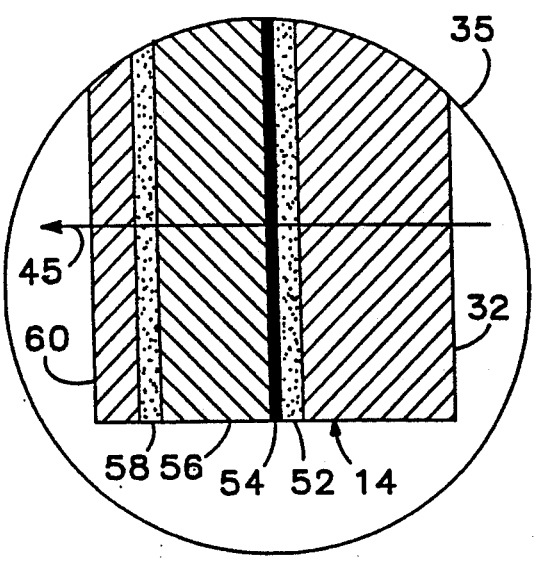
FIG. 4 is an enlarged, cross sectional view of the multi-layered screen component of FIG. 3 illustrating its construction.

Referring now to FIG. 4, providing a close-up view of the region within circle 35 in FIG. 3, screen 14 is comprised of a number of adjacent layers or sheets of material. Light from the EL panel 32 is represented by the light ray 45. In the preferred embodiment, the screen 14 includes five separate layers 52, 54, 56, 58 and 60 arranged in parallel proximity over the EL light source as further described below. First, a generally planar intermediate layer or substrate 56 is formed of a polycarbonate material.

Figure 6A:
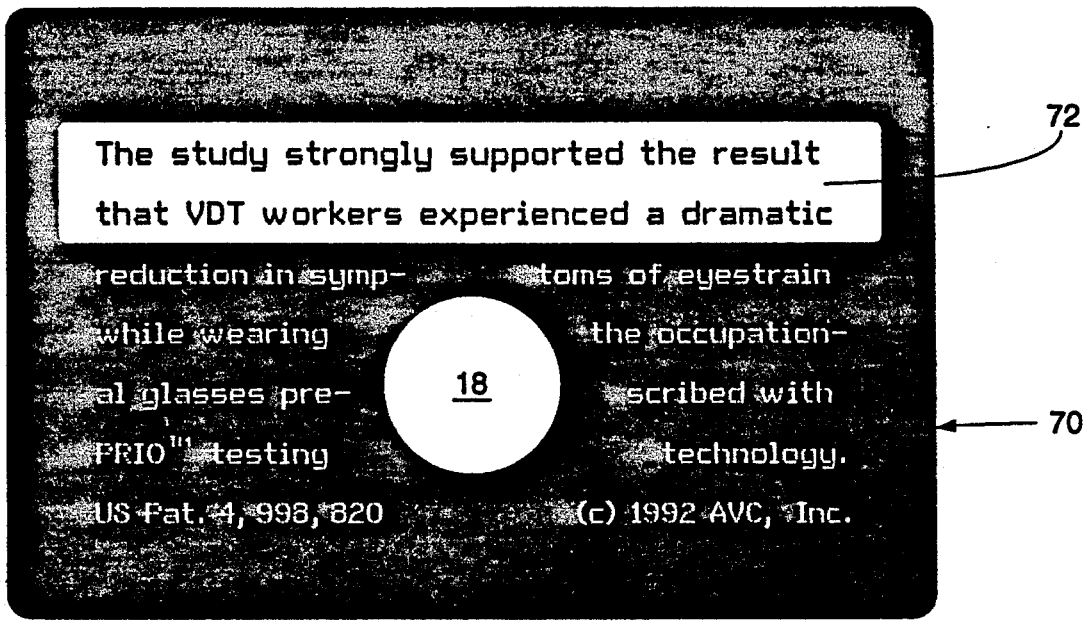
FIG. 6A shows an example of an opaque ink mask useful in constructing the screen of FIG. 4.
Figure 6B:
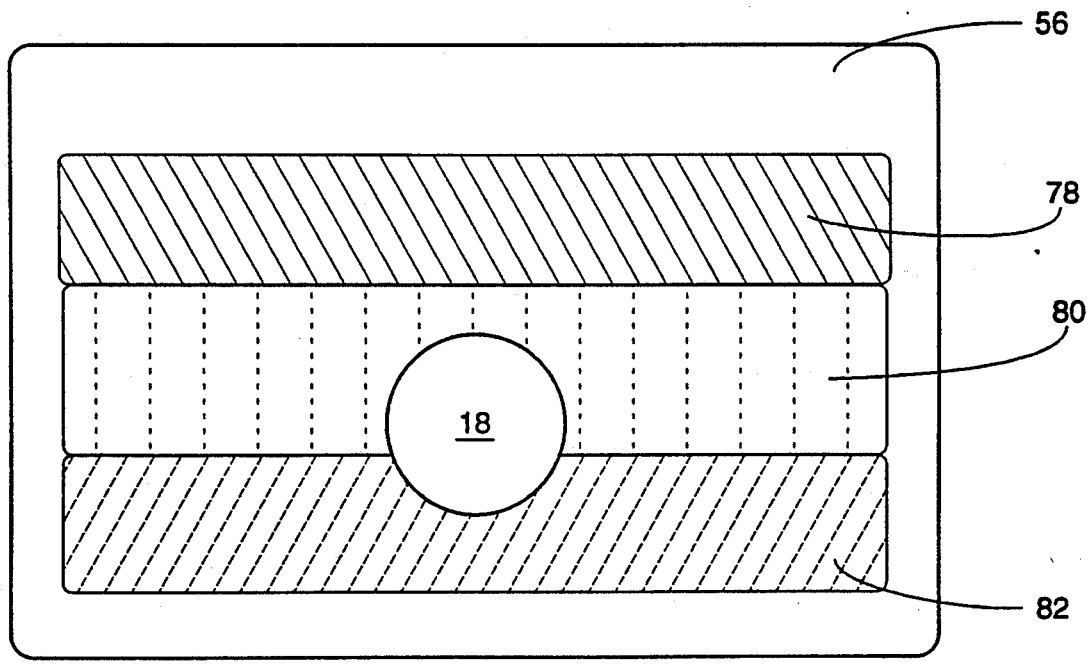
FIG. 6B illustrates an arrangement of multiple tinted ink regions useful for producing a multi-colored screen display image in the tester apparatus of FIGS. 1–4.

Layer 54 comprises an optional translucent layer for color and an opaque mask layer. The color layer, formed of one or more substantially translucent vinyl inks, is applied to one side of the substrate facing the light source for coloring light that passes through the substrate from the light source. Referring to FIG. 6B, the translucent layer may include more than one region, illustrated as regions 78, 80 and 82, each region being formed of an ink having a different color tint and non-overlapping the other regions, so that the resulting screen display exhibits a corresponding color in an area overlying each region.

Preferably, translucent inks are selected so as to be perceived by the patient as a mid-saturation green hue, a mid-saturation yellow-orange (amber) hue, and a low-saturation blue-white hue. These three colors approximate those emitted by the three most commonly used types of VDT screens. Any one of these colors may be used. It is convenient to provide all three of them in a single tester apparatus.

The mask layer, formed of substantially opaque ink, preferably black, is applied to the same side of the substrate over the color layer. The mask layer includes a predetermined pattern of small, circular openings through which colored light is transmitted from the light source toward the patient, for forming an image consisting of pixel-like light elements, each light element formed by one of said openings. See mask layer 70 in FIG. 6A. The various ink layer(s) may be applied to the intermediate substrate by silk screen type printing techniques. In operation, light emitted by the EL panel is colored by one of the tinted ink layers, and blocked by the opaque ink layer except for the pixel openings, through which the light proceeds to the other screen layers.

A cover layer 60 of the screen 14 comprises a 0.010 inch sheet of a polycarbonate plastic functioning as a cover and providing an anti-glare surface for the screen 14. The exterior surface of the outer layer 60 carries a satin matte texture, which also contributes to the desired effect. The layer 60 is selected to be of sufficient thickness to function in combination with other layers 52, 56, and 58 to attenuate the light forming the characters 22 to the extent required to provide approximately a 3 to 1 contrast ratio between the characters and their surrounding background in a manner similar to the contrast found in VDTs. The contrast may also be adjusted by varying the intensity of the light source 28.

The screen further includes a first bonding layer (52) disposed intermediate the EL panel (50) and the intermediate polycarbonate layer (56). The first bonding layer has a substantially lower index of refraction than the intermediate polycarbonate layer (56), for refracting light transmitted through the ink mask pixel openings so as to reduce higher-order spacial frequencies of said transmitted light.

Similarly, the screen further includes a second bonding layer (58) disposed intermediate the cover layer (60) and the intermediate polycarbonate layer (56), the second bonding layer also having a substantially lower index of refraction than the polycarbonate layer (56), for refracting light transmitted through the pixel means so as to reduce higher-order spacial frequencies. Layers 52 and 58 may comprise, for example, 2 mil acrylic adhesive (suitably 3M #967), and have a substantially lower index of refraction than the layer 56, leading to certain desirable optical effects hereinafter described.

Referring once again to FIG. 6A, the mask layer 70 may include a reverse image region 72, in which the opaque ink is generally absent, except for selected dots of ink, the dots being arranged in a predetermined pattern so as to form a desired image such as alphanumeric characters. In this case, the translucent ink layer in the region underlying the reverse image region of the mask layer, i.e. in translucent region 78 in FIG. 6B, has a pale blue tint so that the image as displayed to the patient simulates a black-on-white type of VDT display image.

Printed characters produce a square-wave light amplitude curve as illustrated in FIG. 5A, if the character is scanned across, and the light amplitude curve is scanned across, and the light amplitude curve of prior art devices which rely on printed pixels to simulate a crt is substantially the same. FIG. 5B is a graph of a Gaussian light amplitude output provided by a video display terminal, and by the present invention. This curve may be generated by scanning an actual crt pixel with a micro scan light meter and corresponds to the following formula:

$$f(x) = exp\left[-(41_n^2 x^2)/s^2\right]$$

where $1_n$ is the luminance of the pixel, S is the width of the pixel at half luminance maximum and X is the x-axis position of the meter.

Performing Fourier analysis then provides the amplitude and fundamental frequency of each function. The optical properties of each screen layer (for example as illustrated in FIG. 4) are known or may be determined based upon the material and thickness. The layer combination should have a Fourier transform which matches that actually measured for a selected crt.

In operation, the exemplary design of the screen 14 illustrated in FIG. 3 provides optically unique characteristics on two levels. First, the pixels incorporated into the printer layer 54 allows the characters 22 to be formed from corresponding elements of light as transmitted through the screen 14. The characters 22 are thereby constructed of pixel-like elements of light in a manner analogous to characters displayed on VDTs.

Second, since the layers 52 and 58 provide a lower index of refraction than the layers 56 and 60, the arrangement of these layers forms a lensing structure which operates to refract the light of the elements forming the characters 22 and reduce the higher order spatial frequencies associated with the light elements. Diffraction also occurs at the juncture of the polycarbonate plastic 60 and the adhesive 52, 58, scattering the light. The layers refract the light to a known degree, and the combination thereof provides the desired Gaussian light amplitude.

The light elements forming the characters 22 are effectively defocused, wherein the borders of the characters 22 are "blurred" for degrading the quality of image provided by the apparatus 10. The layers are selected to provide amounts of refraction sufficient to transform the spatial distribution of the light comprising the individual pixel elements into Gaussian type profiles when viewed from a distance of approximately 50 cm from the screen 14, such Gaussian profiles being very similar to the Gaussian type profiles characteristic of the pixels generated by the VDTs. The characters generated by VDTs are thus simulated in two important respects: through the use of pixel-like light elements, and by providing elements having an appropriately degraded image quality, employing a non-complex layer construction.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

We claim:

1. A vision tester for use in conducting optometric examinations of patients who use video display terminals, said system comprising:
   a light source;
   a substantially transparent, generally planar substrate having first and second sides, the first side exposed to the light source;
   a mask layer of substantially opaque ink applied to the first side of the substrate, the mask layer having a predetermined pattern of small, circular openings through which light is transmitted from the light source toward the patient, for forming an image consisting of pixel-like light elements, each light element formed by one of said openings; and
   means disposed between the mask layer and the patient for degrading the quality of the image provided by said light elements by selectively reducing the higher order spatial frequencies associated with the light transmitted through said openings so that light elements transmitted to the patient exhibit a generally Gaussian light amplitude curve for simulating a VDT screen image.

2. A vision tester according to claim 1 wherein the light source comprises a substantially flat electroluminescent panel for providing uniform illumination without a diffusion layer overlying the light source.

3. A vision tester according to claim 2 further comprising a battery pack for providing portable DC power and an inverter circuit coupled to receive the DC power for providing AC power to drive the electroluminescent panel.

4. A vision tester according to claim 1 further comprising a layer of substantially translucent ink applied to the first side of the substrate for coloring light that passes through the substrate from the light source.

5. A vision tester according to claim 4 wherein:
   the translucent ink layer comprises a first region of ink having a first color and a second region of ink of a second color, the second region non-overlapping the first region; and
   the mask layer of opaque ink includes a first pattern of openings positioned over the first region of the translucent ink layer and a second pattern of openings positioned over the second region, so that a first image formed by the first pattern exhibits a first color determined by the first region ink color and a second image formed by the second pattern exhibits a second color determined by the second region ink color, whereby the vision tester displays at least two different colored images for simulating two different types of VDT.

6. A vision tester according to claim 4 wherein the translucent ink layer includes a region of ink tinted so that light transmitted through the translucent ink layer from the light source is perceived by a normal human eye as having a mid-saturation green hue whereby the tester simulates a green background type of VDT screen.

7. A vision tester according to claim 5 wherein:
   the translucent ink layer comprises a third region of ink having a third color different from the first and second colors, the third region non-overlapping the first and second regions; and
   the mask layer of opaque ink includes a third pattern of openings positioned over the third region of the translucent ink layer whereby the tester apparatus simultaneously simulates three different types of video displays.

8. A vision tester according to claim 4 wherein the translucent ink layer includes a region of ink tinted so that light transmitted through the translucent ink layer from the light source is perceived by a normal human eye as having a mid-saturation yellow-orange hue whereby the tester simulates an amber background type of VDT screen.

9. A vision tester according to claim 4 wherein:
   the mask layer includes a reverse image region in which the opaque ink is generally absent, except for selected dots of ink, the dots being arranged in a predetermined pattern so as to form the image; and
   the translucent ink in a region underlying the reverse image region of the mask layer is a pale blue color so that the image as displayed to the patient simulates a black-on-white type of VDT display image.

10. A vision tester apparatus comprising:
    a generally flat, rigid housing (16) having front and back sides;

a flat electroluminescent panel light source (32) disposed within the housing for providing illumination toward the front of the housing;

a substantially transparent planar screen (14) disposed within the housing over the electroluminescent panel so that the electroluminescent panel illuminates the screen; and a mask layer of substantially opaque ink applied to the screen, the mask layer having a predetermined pattern of small, circular openings through which light is transmitted from the light source toward a patient, for forming an image consisting of pixel-like light elements, each light element formed by one of said openings, for simulating a VDT screen image.

11. A vision tester apparatus according to claim 10 wherein:

the housing includes a central viewing tunnel (18) extending between the front and back sides;

the EL panel includes a central aperture registered with the viewing tunnel; and the screen includes a central aperture also registered with the viewing tunnel, whereby a user can observe a patient while the tester is in use by peering through the viewing tunnel from the back side of the housing.

12. A vision tester apparatus according to claim 10 further comprising a support arm (20) coupled to the housing (16) for supporting the housing so as to present the screen to a patient; and means for rotating the housing about a vertical axis, whereby either one of the front and back sides of the housing may be presented to a patient as desired without adjusting the support arm.

13. A vision tester apparatus according to claim 10 further comprising a printed eye-chart mounted onto the back side of the housing, so that the eye-chart may be used by reversing the tester orientation relative to a patient.

14. An optical system according to claim 10 wherein the screen includes a polycarbonate cover layer (60) and an intermediate polycarbonate layer (56) interposed between the EL panel and the polycarbonate cover layer; and wherein the mask layer of ink is formed on a surface of the intermediate polycarbonate layer (56) facing the EL panel.

15. An optical system according to claim 14 wherein the screen further includes a first bonding layer (52) disposed intermediate the EL panel (50) and the intermediate polycarbonate layer (56), the first bonding layer having a substantially lower index of refraction than the intermediate polycarbonate layer (56), for refracting light transmitted through the ink mask pixel openings so as to reduce higher-order spacial frequencies of said transmitted light.

16. An optical system according to claim 15 wherein the intermediate polycarbonate layer is coated with a thin layer of a substantially transluscent, tinted ink so as to color light transmitted through the said layer for simulating a color of a video display terminal.

17. A vision tester according to claim 16 wherein the screen includes:

lensing means for refracting the light elements and reducing higher order spacial frequencies in the light elements such that the light elements exhibit a substantially Gaussian light amplitude curve to the patient to emulate light emitted by pixels in a VDT.

18. A vision tester apparatus comprising:

a generally flat, rigid housing (16) having front and back sides;

a flat electroluminescent panel light source (32) disposed within the housing for providing illumination toward the front of the housing;

a substantially planar screen disposed within the housing over the electroluminescent panel so that the electroluminescent panel illuminates the screen;

a bezel (16) extending generally along a periphery of the front of the housing overlapping a periphery of the screen (14) and coupled to the housing (16) so as to secure the screen in place within the housing; and power means (34) in the housing coupled to the electroluminescent panel for powering the electroluminescent panel to illuminate the screen;

the screen including;

a polycarbonate cover layer (60) and an intermediate polycarbonate layer (56) interposed between the electroluminescent panel and the polycarbonate cover layer; and a thin ink mask (54) formed on a surface of the intermediate polycarbonate layer (56) facing the electroluminescent panel, the ink mask comprising a layer of substantially opaque ink (70) and having a plurality of pixel openings in it for transmitting light from the electroluminescent panel through the intermediate polycarbonate layer and the polycarbonate cover layer so as to form corresponding pixels (24) as seen by a patient facing the screen.

19. An optical system according to claim 18 wherein the screen further includes a first bonding layer (52) disposed intermediate the electroluminescent panel (50) and the intermediate polycarbonate layer (56), the first bonding layer having a substantially lower index of refraction than the intermediate polycarbonate layer (56), for refracting light transmitted through the ink mask pixel openings so as to reduce higher-order spacial frequencies of said transmitted light.

20. An optical system according to claim 19 wherein the screen further includes a second bonding layer (58) disposed intermediate the cover layer (60) and the intermediate polycarbonate layer (56), the second bonding layer having a substantially lower index of refraction than the polycarbonate layer (56), for refracting light transmitted through the pixel means so as to reduce higher-order spacial frequencies.

21. An optical system according to claim 20 wherein the polycarbonate cover layer (60), intermediate polycarbonate layer (56) and first and second bonding layers are selected to have optical properties such that in combination they provide the refracting means to reduce higher-order spacial frequencies so that light transmitted from the light source through the screen to the patient exhibits a substantially Gaussian light amplitude curve.

22. An optical system according to claim 18 wherein the intermediate polycarbonate layer is coated with a thin layer of a substantially translucent, tinted ink so as to color light transmitted through the said layer for simulating a color of a video display terminal.

23. A vision tester for use in conducting optometric examinations a patient who uses video display terminals, comprising:

a generally flat, rigid housing (16) having front and back sides;

a flat electroluminescent panel light source (32) disposed within the housing for providing illumination toward the front of the housing;

a substantially planar screen (14) disposed within the housing over the electroluminescent panel so that the electroluminescent panel illuminates the screen;

a bezel (16) extending generally along a periphery of the front of the housing overlapping a periphery of the screen (14) and coupled to the housing (16) so as to secure the screen in place within the housing; and power means (34) in the housing coupled to the electroluminescent panel for powering the electroluminescent panel to illuminate the screen;

the screen including:

means for defining a predetermined pattern of small, circular openings through which light travels from the light source toward the patient as pixel-like light elements, each light element being formed by one of said openings, for simulating VDT pixels; and lensing means for refracting the light elements and reducing higher order spacial frequencies in the light elements such that the light elements exhibit a substantially Gaussian light amplitude curve to the patient to emulate light emitted by pixels in a VDT.

24. A vision tester apparatus according to claim 23 wherein the means for defining a pattern of openings includes a layer of ink applied to the screen.

25. An optical display method for use in conducting optometric examinations comprising:

providing a flat-panel electroluminescent light source for illumination substantially without hot spots;

coloring light emitted by the electroluminescent light source;

transmitting the colored light through a screen having sets of openings which function to cooperatively define a predetermined image in terms of pixel-like light elements; and degrading the quality of the image formed by the light elements by reducing higher order spatial frequencies associated with the colored light transmitted through said openings so that light elements transmitted from the light source through the screen to a patient exhibit a generally Gaussian light amplitude curve for simulating a video display terminal image.

26. An optical display method for use in conducting optometric examinations comprising:

providing a flat-panel electroluminescent light source for illumination substantially without hot spots;

transmitting light emitted by the electroluminescent light source through a screen having sets of openings which function to cooperatively define a predetermined image in terms of pixel-like light elements; and degrading the image formed by the light elements by reducing higher order spatial frequencies associated with the light transmitted through said openings so that light elements transmitted from the light source through the screen exhibit a generally Gaussian light amplitude curve for simulating a video display terminal image.

* * * * *